(12) United States Patent
Zenz et al.

(10) Patent No.: US 7,247,767 B2
(45) Date of Patent: Jul. 24, 2007

(54) MOUSE MODEL FOR PSORIASIS AND PSORIATIC ARTHRITIS

(75) Inventors: Rainer Zenz, Graz (AT); Erwin Wagner, Vienna (AT)

(73) Assignee: Boehringer Ingelheim International GmbH (DE)

(*) Notice: Subject to any disclaimer, the term of this patent is extended or adjusted under 35 U.S.C. 154(b) by 0 days.

(21) Appl. No.: 11/038,387

(22) Filed: Jan. 21, 2005

(65) Prior Publication Data

US 2005/0268348 A1 Dec. 1, 2005

Related U.S. Application Data

(60) Provisional application No. 60/548,426, filed on Feb. 27, 2004.

(30) Foreign Application Priority Data

Jan. 21, 2004 (EP) ................... 04001181

(51) Int. Cl.
*A01K 67/027* (2006.01)
*G01N 33/00* (2006.01)
(52) U.S. Cl. .......................... 800/18; 800/3
(58) Field of Classification Search .............. 800/9, 800/18

See application file for complete search history.

(56) References Cited

FOREIGN PATENT DOCUMENTS

| WO | WO 96/27019 | 9/1996 |
|----|-------------|--------|
| WO | WO 00/12754 | 3/2000 |
| WO | WO 00/72666 | 12/2000 |
| WO | WO 01/22090 | 3/2001 |
| WO | WO 02/062135 | 8/2002 |

OTHER PUBLICATIONS

Szabowski et al. Cell 103:745-755, 2000; of record.*
Li et al. Developmental Cell 4:865-877, 2003; of record.*
Vasioukhin et al. PNAS 96:8551-8556, 1999; of record.*
Zenz et al. Nature 437: 369-375; 2005.*
Baichwal, V.R., and Tjian, R., "Control of c-Jun Activity by Interaction of a Cell-Specific Inhibitor with Regulatory Domain δ: Differences between v- and c-Jun," *Cell* 63:815-825, Cell Press (1990).
Behrens, A., et al., "Impaired postnatal hepatocyte proliferation and liver regeneration in mice lacking c-*jun* in the liver," *EMBO J.* 21:1782-1790, Oxford University Press (2002).
Bohmann, D., and Tjian, R., "Biochemical Analysis of Transcriptional Activation by Jun: Differential Activity of c- and v-Jun," *Cell* 59: 709-717, Cell Press (1989).
Boyle, W.J., et al., "Activation of Protein Kinase C Decreases Phosphorylation of c-Jun at Sites That Negatively Regulate Its DNA-Binding Activity," *Cell* 64: 573-584, Cell Press (1991).
Branda, C.S., and Dymecki, S.M., "Talking about a Revolution: The Impact of Site-Specific Recombinases on Genetic Analyses in Mice," *Dev. Cell* 6:7-28, Cell Press (Jan. 2004).

Brocard, J., et al., "Spatio-temporally controlled site-specific somatic mutagenesis in the mouse," *Proc. Natl. Acad. Sci. USA* 94:14559-14563, National Academy of Sciences (1997).
Carroll, J.M., and Molés, J-P., "A three-dimensional skin culture model for mouse keratinocytes: application to transgenic mouse keratinocytes," *Exp. Dermatol.* 9:20-24, Munskgaard (2000).
Carroll, J.M., et al., "Suprabasal Integrin Expression in the Epidermis of Transgenic Mice Results in Developmental Defects and a Phenotype Resembling Psoriasis," *Cell* 83: 957-968, Cell Press (1995).
Chiu, R., et al., "Jun-B Differs in Its Biological Properties from, and Is a Negative Regulator of, c-Jun," *Cell* 59:979-986, Cell Press (1989).
Danielian, P.S., et al., "Identification of Residues in the Estrogen Receptor That Confer Differential Sensitivity to Estrogen and Hydroxytamoxifen," *Mol. Endocrinol.* 7:232-240, Endocrine Society (1993).
Deng, T., and Karin, M., "JunB differs from c-Jun in its DNA-binding and dimerization domains, and represses c-Jun by formation of inactive heterodimers," *Genes Dev.* 7:479-490, Cold Spring Harbor Laboratory Press (1993).
Du, W., et al., "Mechanims of Transcriptional Synergism between Distinct Virus-Inducible Enhancer Elements," *Cell* 74: 887-898, Cell Press (1993).
Eferl, R., and Wagner, E.F., "AP-1: A Double-Edged Sword in Tumorigenesis," *Nat. Rev. Cancer* 3:859-868, Nature Publishing Group (Nov. 2003).
Herrlich, P., and Ponta, H., "'Nuclear' Oncogenes Convert Extracellular Stimuli into Changes in the Genetic Program," *Trends Genet.* 5:112-116, Elsevier Science Publisher Ltd. (1989).
Hilberg, F., et al., "c-Jun is essential for normal mouse development and hepatogenesis," *Nature* 365: 179-181, Macmillan Magazines Ltd. (1993).
Imler, J.L., et al., "v-jun is a transcriptional activator, but not in all cell-lines," *Nucleic Acids Res.* 16:3005-3012, IRL Press Ltd. (1988).
Jiang, C-K., et al., "Functional Comparison of the Upstream Regulatory DNA Sequences of Four Human Epidermal Keratin Genes," *J. Invest. Dermatol.* 96:162-167, Elsevier Science Publishing Co., Inc. (1991).
Johnson, R.S., et al., "A null mutation at the c-*jun* locus causes embryonic lethality and retarded cell growth in culture," *Genes Dev.* 7:1309-1317, Cold Spring Harbor Laboratory Press (1993).
Karin, M., and Smeal, T., "Control of transcription factors by signaling transduction pathways: the beginning of the end," *Trends. Biochem. Sci.* 17:418-422 Elsevier Science Publishers (1992).

(Continued)

*Primary Examiner*—Anne Maria S. Wehbe
*Assistant Examiner*—Fereydoun G. Sajjadi
(74) *Attorney, Agent, or Firm*—Sterne, Kessler, Goldstein & Fox P.L.L.C.

(57) ABSTRACT

A mouse that is deficient for c-Jun and JunB in the epidermis or in which deletion of c-Jun and JunB can be specifically induced in the epidermis, and methods for obtaining such mice. The mice and keratinocytes derived therefrom are useful as an animal model for psoriasis and psoriatic arthritis.

19 Claims, 7 Drawing Sheets

OTHER PUBLICATIONS

Kenner, L., et al., "Mice lacking JunB are osteopenic due to cell-autonomous osteoblast and osteoclast defects," *J. Cell Biol.* 164:613-623, Rockefeller University Press (Feb. 2004).

Kunath, T., et al., "Transgenic RNA interference in ES cell-derived embryos recapitulates a genetic null phenotype," *Nat. Biotechnol.* 21:559-561, Nature Publishing Group (May 2003).

Lebwohl, M., "Psoriasis," *Lancet 361*:1197-1204, Lancet Publishing Group (Apr. 2003).

Li, B., et al., "Regulation of IL-4 expression by the transcription factor JunB during T helper cell differentiation," *EMBO J.* 18:420-432, Oxford University Press (1999).

Li, G., et al., "c-Jun Is Essential for Organization of the Epidermal Leading Edge," *Dev. Cell 4*:865-877, Cell Press (Jun. 2003).

Lin, A., et al., "Casein Kinase II is a Negative Regulator of c-Jun DNA Binding and AP-1 Activity," *Cell 70*:777-789, Cell Press (1992).

Minamino, T., et al., "Inducible Gene Targeting in Postnatal Myocardium by Cardiac-Specific Expression of a Hormone-Activated Cre Fusion Protein," *Circ Res.* 88:587-592, Lippincott Williams & Wilkins (2001).

Nickoloff, B.J., et al., "Is psoriasis a T-cell disease?" *Exp. Dermatol.* 9: 359-375, Munksgaard (2000).

Pulverer, B.J., et al., "Phosphorylation of c-*jun* mediated by MAP kinases," *Nature 353*:670-674, Macmillan Magazines Ltd. (1991).

Ransone, L.J., and Verma, I.M., "Nuclear Proto-Oncogenes *Fos* and *Jun*," *Annu. Rev. Cell Biol.* 6:539-557, Annual Reviews, Inc. (1990).

Sachsenmaier, C., and Radler-Pohl, A., "Regulation of c-Jun Activity by Phosphorylation," in *The FOS and JUN Families of Transcription Factors*, Angel, P.E., and Herrlich, P.A., eds., CRC Press Inc., Boca Raton, FL, pp. 61-70 (1994).

Schön, M.P., "Animal Models of Psoriasis—What Can We Learn from Them?" *J. Invest. Dermatol.* 112:405-410, Blackwell Science (1999).

Schorpp-Kistner, M., et al., "JunB is essential for mammalian placentation," *EMBO J.* 18:934-948, Oxford University Press (1999).

Stein, B., et al., "Cross-coupling of the NF-κB p. 65 and Fos/Jun transcription factors produces potentiated biological function," *EMBO J.* 12:3879-3891, Oxford University Press (1993).

Szabowski, A., et al., "c-Jun and JunB Antagonistically Control Cytokine-Regulated Mesenchymal-Epidermal Interaction in Skin," *Cell 103*:745-755, Cell Press (2000).

Vasioukhin, V., et al., "The magical touch: Genome targeting in epidermal stem cells induced by tamoxifen application to mouse skin," *Proc. Natl. Acad. Sci. USA 96*:8551-8556, National Academy of Sciences (1999).

Xia, H., et al., "siRNA-mediated gene silencing in vitro and in vivo," *Nat. Biotechnol.* 20:1006-1010, Nature Publishing Group (2002).

Xia, Y-P., et al., "Transgenic delivery of VEGF to mouse skin leads to an inflammatory condition resembling human psoriasis," *Blood 102*:161-168, American Society of Hematology (Jul. 2003).

Zenz, R., et al., "c-Jun Regulates Eyelid Closure and Skin Tumor Development through EGFR Signaling," *Dev. Cell 4*:879-889, Cell Press (Jun. 2003).

International Search Report for International Application No. PCT/EP2005/000517, European Patent Office, Netherlands, mailed on Jun. 2, 2005.

Angel, P., et al., "Function and regulation of AP-1 subunits in skin physiology and pathology," *Oncogene 20*: 2413-2423, Nature Publishing Group (2001).

Angel, P. amd Herrlich, P., "General Structure of AP-1 Subunits and Characteristics of the Jun Proteins," in *The fos and jun families of transcription factor*, CRC Press, Inc., pp. 3-14 (1994).

Werner, S. and Smola, H., "Paracrine Regulation of Keratinocyte Proliferation and Differentation," *Trends Cell Biol.* 11:143-146, Elsevier Science Ltd. (2001).

European Search Report for European Application No. EP 04 00 1181, European Patent Office, Netherlands, mailed on Jul. 8, 2004.

\* cited by examiner

| c-jun$^{f/f}$; junB$^{f/f}$ | c-jun$^{\Delta ep*}$; junB$^{\Delta ep*}$ |
|---|---|
|  |  |
|  |  |
|  |  |

Figure 2B

Figure 2C finger — joint c-jun$^{\Delta ep*}$; junB$^{\Delta ep*}$

US 7,247,767 B2

MOUSE MODEL FOR PSORIASIS AND PSORIATIC ARTHRITIS

This patent application claims priority to provisional patent application No. 60/548,426 filed Feb. 27, 2004, which is hereby incorporated herein by reference.

BACKGROUND OF THE INVENTION

1. Field of the Invention

The invention relates to the field of psoriasis.

2. Background Art

Psoriasis, affecting about 2% of the population, is one of the most common human skin disorders that affect skin and joints. It is characterized by complex alterations of various cell types. This includes epidermal hyperproliferation and altered differentiation, as well as angiogenesis and dilation of dermal blood vessels (Schön, 1999; Lebwohl, 2003). In addition, a mixed leukocytic infiltrate is seen. It is composed of activated T lymphocytes, neutrophiles within the dermis and epidermal microabscesses, lining macrophages, and an increased number of dermal mast cells. Cytokines including tumor necrosis factor-$\alpha$ (TNF-$\alpha$), and interleukin-1 (IL-1), interferon-$\gamma$ (INF-$\gamma$), IL-6, IL-8, vascular endothelial growth factor (VEGF) and transforming growth factor-$\alpha$ (TGF-$\alpha$) are thought to mediate the psoriatic tissue alterations (Schön, 1999).

For decades the ongoing controversy is whether psoriasis results from primary abnormalities in the epidermis or is immunologically based (Nickoloff et al., 2000). Although evidence is accumulating that it has an immunological basis others interpret psoriasis as a genetically determined, abnormal epithelial response pattern to infection and/or physicochemical skin insults.

It has become clear that psoriatic skin is a hotbed of epidermal growth factors and inflammatory mediators. Supportive evidence of a key role for such mediators comes from patients who respond to immunsuppressive, anti-inflammatory, and antiproliferative therapies such as cyclosporine, methotrexate, tacrolimus, corticosteroids, and ultraviolet-light-activated psoralen. However, extensive efforts aimed at transgenically delivered inflammatory mediators or keratinocyte growth factors to the skin have not completely reproduced the psoriatic phenotype (Xia et al., 2003), which has thus far only been faithfully modeled in animals by transplanting psoriatic skin onto mice with severe combined immunodeficiency disease (SCID). So far no reported mouse model for psoriasis mimics all characteristics seen in psoriasis in humans, including psoriatic arthritis which is present in up to 40% of psoriasis patients.

Since there is no naturally occurring animal skin disease mirroring both phenotype and immunopathogenesis of psoriasis, research into the pathogenesis of this common skin disorder has been severely hampered.

Consequently, there is a need for an efficient and significant animal model for the study of psoriasis and for testing drug candidates effective in the treatment of this disorder.

BRIEF SUMMARY OF THE INVENTION

It was an object of the invention to provide an animal model for psoriasis, including psoriatic arthritis.

In a first aspect, the invention relates to a mutant mouse which is deficient for c-Jun and JunB in the epidermis ($jun^{\Delta ep^*}, junB^{\Delta ep^*}$).

In a preferred embodiment, the deficiency of c-Jun and JunB is caused by a deletion of c-Jun and JunB achieved by expression of a constitutively active or inducible recombination enzyme in the epidermis.

In a further aspect, the invention relates to a mutant mouse, in which deletion of c-Jun and JunB can be specifically induced in the epidermis.

In a preferred embodiment, deletion of c-Jun and JunB is achieved by expression of a constitutively active or inducible recombination enzyme in the epidermis.

In a further aspect, the present invention relates to a mutant mouse which is deficient for c-Jun and JunB.

In an additional aspect, the present invention relates to a method for producing a mutant mouse that is deficient for c-Jun and JunB in the epidermis comprising crossing (a) a transgenic mouse comprising a genetic construct containing the c-Jun and JunB genes flanked with recognition sites for a site-specific recombination enzyme with (b) a transgenic mouse expressing a constitutively active or inducible recombinase in the epidermis, wherein deletion of c-Jun and JunB is specifically induced in the epidermis.

In one embodiment, the deficiency of c-Jun and JunB in the epidermis of the mutant mouse is induced by applying an anti-estrogen. The anti-estrogen is applied by intraperitoneal injection or by topical application. An example of a suitable anti-estrogen is tamoxifen.

In a further aspect, the present invention relates to a method for producing a mutant mouse in which deletion of c-Jun and JunB can be specifically induced in the epidermis comprising crossing (a) a transgenic mouse comprising a genetic construct containing the c-Jun and JunB genes flanked with recognition sites for a site specific recombination enzyme with (b) a transgenic mouse expressing a constitutively active or inducible recombinase in the epidermis.

In one embodiment, the epidermal cells in the mutant mouse comprise a genetic construct comprising a keratinocyte-specific promoter operably linked to a nucleic acid molecule encoding Cre-recombinase, wherein said promoter is also operably linked to an estrogen receptor.

In another embodiment of the invention, isolated keratinocytes may be derived from the mutant mouse that is either deficient for c-Jun and JunB in the epidermis or the mutant mouse in which deletion of c-Jun and JunB can be specifically induced in the epidermis.

Furthermore, the present invention is directed to the method of testing a drug to treat psoriasis in a human comprising administration of the drug to the mutant mouse that is deficient for c-Jun and JunB in the epidermis. Additionally, the present invention is directed to the method of testing a drug to treat psoriatic arthritis in a human comprising administration of the drug to the mutant mouse in which deletion of c-Jun and JunB can be specifically induced in the epidermis.

BRIEF DESCRIPTION OF THE DRAWINGS

FIG. 1

A.) Schematic outline of the floxed c-jun and floxed junB locus and the inducible Cre-ER transgene used to delete both genes upon tamoxifen application.

B.) Treatment scheme. Adult mice were injected intraperitoneally 5 times with 1 mg tamoxifen and analyzed 14 days thereafter.

C.) Southern Blot for c-jun and junB to confirm deletion of both genes after tamoxifen application specifically in the epidermis of adult mice.

D.) RPA (RNAse protection assay) for AP-1 genes after deletion of c-jun and junB demonstrating downregulation of all AP-1 genes beside fra-2.

FIG. 2

A.) Macroscopy of ear, feet and tail from adult mice after inducible deletion of c-jun and junB in the epidermis of adult mice resembling psoriasis.

B.) Histology of psoriatic mouse ears reflecting the hallmarks of psoriasis: abnormally thickened epidermis, parakeratosis (nucleated keratinocytes in the cornified layer), thickened keratinized upper layer (hyperkeratosis), and fingerlike epidermal projections into the dermis (rete ridges). Epidermal microabscesses and the typical inflammatory cell infiltrate are seen: intraepidermal T-cells (CD3 staining), increased numbers of neutrophils in the epidermis (esterase staining), and macrophages in the dermis (esterase- and F4/80-staining).

C.) H&E staining from affected mouse finger demonstrating granulocytic infiltrates into the joint region similar to psoriatic arthritis.

DETAILED DESCRIPTION OF THE INVENTION

The solution of the problem underlying the invention is based on the molecular mechanisms associated with the transcription factor AP-1.

The transcription factor AP-1 is generated by a series of dimers of products of the Fos, Jun, and CREB/ATF protein families (Eferl and Wagner, 2003), as well as other bZip proteins. In addition, associations have been observed between Fos or Jun and the p65 subunit of NFκB (Stein et al., 1993), and ATF-2 and p50-NFκB (Du et al., 1993). Combinatorial association can draw on three Jun genes (c-jun, junB, junD), four Fos genes (c-fos, fosB, fra-1, fra-2) and several CREB/ATF genes. Despite the high degree of homology in the overall structural features, the different members of the Fos, Jun and CREB families exhibit significant differences, which lead to subtle differences in DNA binding and transcriptional activation (Angel and Herrlich, 1994) suggesting specific functions in gene regulation for individual dimers. The members of the AP-1 family are engaged in the control of cell proliferation as well as various types of differentiation, and also in neural function and stress responses. AP-1 is one of the key factors that translate external stimuli both into short- and long-term changes of gene expression.

The transcription factor c-Jun interacts with related and unrelated transcription factors, gaining influence on different and seemingly unrelated signal pathways controlling diverse target genes. c-Jun receives regulatory input originating outside of the cell, traversing the plasma membrane, cytoplasm, and nuclear envelope in a cascade of biochemical reactions (Herrlich and Ponta, 1989; Ransone and Verma, 1990; Karin and Smeal, 1992). These signals can modify the transcription of the c-jun gene or affect the activity of the c-Jun protein post-translationally. The regulation of c-Jun's transactivation potential takes place at two different levels: increased phosorylation in the transactivation domain causes enhanced transcriptional activity, and enhanced binding to DNA is due to dephosphorylation in the DNA binding region (Sachsenmaier and Radler-Pohl, 1994). Unstimulated mammalian cells contain low, but detectable, amounts of c-Jun protein. In this state c-Jun is phosphorylated constitutively at serines and threonines close to its C-terminal DNA binding domain. Phosporylation in this region markedly reduces DNA binding and transactivation ability of c-Jun in vitro (Boyle et al., 1991) and in vivo (Lin et al., 1992). In contrast to the negative effect of hyperphosphorylation in DNA binding, enhanced phosphorylation at the N-terminus is required for the activation of the transactivation function of c-Jun. Serines 73 and 63 are located close to a stretch of amino acids described as the "proline-rich region", which is required for transactivation and can serve as in vitro substrates for mitogen-activated protein (MAP) kinases (Pulverer et al., 1991). Transcriptional regulation by c-Jun is highly cell type dependent (Imler et al., 1988; Bohmann and Tjian, 1989; Baichwald and Tjian, 1990), because of different upstream activators, partner molecules, or downstream targets present in the different cell types. A functional role for c-Jun in the skin has been suggested for differentiation and carcinogenesis. Since c-jun knock-out mice are not viable (Johnson et al., 1993; Hilberg et al., 1993), the consequence of lacking c-Jun in skin development and skin carcinogenesis could only be investigated by generation of conditional c-jun knock-out mice (c-jun$^{\Delta ep}$) (Zenz R. et al., 2003; Li et al., 2003). Mice lacking c-jun in keratinocytes (c-jun$^{\Delta ep}$) develop normal skin but express reduced levels of EGFR in the eyelids, leading to open eyes at birth, as observed in EGFR null mice. Primary keratinocytes from c-jun$^{\Delta ep}$ mice proliferate poorly, show increased differentiation, and form prominent cortical actin bundles, most likely because of decreased expression of EGFR and its ligand HB-EGF. In the absence of c-Jun, tumor-prone K5-SOS-F transgenic mice develop smaller papillomas, with reduced expression of EGFR in basal keratinocytes. Thus, using three experimental systems, we showed that EGFR and HB-EGF are regulated by c-Jun, which controls eyelid development, keratinocyte proliferation, and skin tumor formation.

All the Jun proteins (c-Jun, JunB and JunD) are similar with respect to their primary structure and their DNA-binding specificity. However, JunB, due to a small number of amino acid changes in its basic-leucine zipper region exhibits a 10-fold weaker DNA-binding activity and a decreased homodimerization property compared to c-Jun. Transfection studies have suggested that junB is a repressor of AP-1 mediated transactivation and transformation most likely due to the preferential formation of inactive c-Jun/junB dimers (Chiu et al., 1989; Deng and Karin, 1993). However, in vitro and in vivo data have demonstrated that JunB can also be a strong transactivator depending on both the interacting partner and the promoter context (Chiu et al., 1989; Li et al., 1999).

Since junB knock-out mice are not viable (Schorpp-Kistner et al., 1999), the consequence of lacking JunB in skin development and skin carcinogenesis can only be investigated by generation of conditional junB knock-out mice (junB$^{\Delta ep}$).

Depending on the experimental system, c-Jun and JunB have been thought to have opposite functions in regulating gene expression, thereby influencing the biological output of various external and internal signals triggering AP-1 activity. To verify this, in the experiments leading to the invention, a novel experimental system was used by generating epidermis-specific double knock-out mice that are deficient for both c-jun and junB (c-jun$^{\Delta ep}$, junB$^{\Delta ep}$). Unexpectedly, these mice die shortly after birth preventing the analysis of phenotypes at later stages in the development of these mice.

Therefore, in the experiments of the invention, an inducible conditional knock-out mouse that is deficient for c-jun and junB in the epidermis was generated.

For clarity, the terminology and abbreviations used herein have the following meanings:

c-jun$^{f/f}$; junB$^{f/f}$ or c-jun$^{f/f}$, junB$^{f/f}$, respectively, refers to mice with a floxed c-Jun or junB locus or mice with floxed c-Jun and JunB loci, respectively.

c-jun$^{f/f}$ K5-Cre-ER (or junB$^{f/f}$ K5-Cre-ER or c-jun$^{f/f}$, junB$^{f/f}$ K5-Cre-ER, respectively) refers to the floxed mice, in which the respective gene(s) are not (yet) deleted, since Cre needs to be activated first. Activation of Cre, and consequently deletion of the gene(s), is achieved by applying tamoxifen. (c-jun$^{f/f}$, junB$^{f/f}$ K5-Cre-ER mice are representative for the above-defined mice, in which deletion of c-Jun and JunB can be specifically induced in the epidermis.)

c-jun$^{f/f}$ K5-Cre (or junB$^{f/f}$ K5-Cre or c-jun$^{f/f}$, junB$^{f/f}$ K5-Cre, respectively), refers to mice in which the respective gene(s) have been deleted in the epidermis (Cre is in the active status). c-jun$^{f/f}$, junB$^{f/f}$ K5-Cre mice are representative for the above-defined mice, which are deficient for c-Jun and JunB in the epidermis (such mice are also designated "c-jun$^{\Delta ep^*}$, junB$^{\Delta ep^*}$ mice").

The constituents K5, Cre and ER can be replaced by any other suitable epidermis-specific promoter, recombination enzyme or gene encoding a biological molecule, respectively, which, upon binding of its ligand, induces activation of the recombination enzyme, e.g. another hormone receptor like the progesterone receptor binding domain, which is activated upon binding of an antiprogestin, e.g. RU486 binding (Minamino et al., 2001).

In a further aspect, the invention relates to methods for generating c-jun$^{\Delta ep^*}$, junB$^{\Delta ep^*}$ mice.

The principle of suitable methods is based on known protocols for generating transgenic mice, preferably on embryonic stem (ES) cell technology. The essential features of suitable preferred methods for obtaining the c-jun$^{\Delta ep^*}$, junB$^{\Delta ep^*}$ mice of the invention are, on the one hand, that the c-Jun and JunB genes are flanked with recognition sites for a site specific recombination enzyme (recombinase), and that, on the other hand, the recombinase can be provided by crossing the conditional knock-out mouse with a transgenic mouse expressing a constitutively active or inducible recombinase in the tissue of interest, i.e. the epidermis. Epidermis-specific expression can be achieved by using a promoter specific for skin cells, in particular keratinocytes; examples for suitable promoters are K5, K6, K10 or K14 (Jiang et al., 1991).

In the experiments of the invention, the inducible gene deletion system enabling to delete both genes in adult mice, as described by Vasioukhin et al., 1999), was used. This system allows to prevent postnatal lethality of c-jun$^{\Delta ep}$, junB$^{\Delta ep}$ mice, which would not allow for analysis of phenotypes at later stages in the development. This system uses a K5-Cre-ER transgenic mouse line, which expresses a Cre-recombinase estrogen receptor fusion under the control of the keratinocyte-specific Keratin 5 promoter (K5) specifically in the epidermis. Using this system, both genes in adult mice can be deleted by consecutive intraperitoneal tamoxifen injection (Brocard et at., 1999; Vasioukhin et at., 1999). In keratinocytes expressing the Cre-ER fusion protein tamoxifen, an anti-estrogene, binds to the mutated estrogen receptor domain. This mutated fusion protein does not bind the endogenous 17β-estradiol, whereas it binds the synthetic ligand tamoxifen (Danielian et at., 1993). Tamoxifen binding is inducing a conformational change in the protein structure leading to an active Cre-recombinase. The active Cre-recombinase is transported into the nucleus and deletes the DNA-sequences between 2 loxP sites (floxed gene).

For obtaining the epidermis-specific double knock-out mice of the invention, which are deficient for both c-jun and junB mice, according to a preferred embodiment, the inducible loxP/Cre system is used. To date, this system is considered to be the most reliable experimental setup for spatio-temporally controlled site-specific somatic gene deletion in vivo. The deletion of the gene(s) of interest (in the case of the present invention c-jun and junB) can be induced either by intraperitoneal injection or topic application of an anti-estrogen like tamoxifen or OH-tamoxifen to the skin (Vasioukhin et al., 1999).

Alternatively to the loxP/Cre-system, other spatio-temporally controlled site-specific somatic gene deletion systems can be used to generate epidermis-specific double knock-out mice for c-jun and junB.

Examples for such alternative methods for engineering the conditional knock-out mice of the invention are the Flp-FRT and the phiC31-att site-specific recombinase systems. As the loxP/Cre-system, these systems fulfill the requirements of having the gene(s) of interest flanked with recognition sites for the site specific recombination enzyme and of providing the recombination enzyme by crossing the conditional knock-out mouse with a transgenic mouse expressing a constitutively active or inducible recombinase in the tissue of interest (Branda and Dymecki, 2004).

Alternatively to spatio-temporally controlled site-specific somatic gene deletion systems, siRNA techniques can be used for skin-specific gene silencing.

Recently, plasmid-based systems using RNA-polymerase III promoters to drive short hairpin RNA (shRNA) molecules have been established to produce siRNA and the generation of knockdown ES cell lines with transgenic shRNA was reported (Kunath et al., 2003). Furthermore, viral-mediated delivery for specific silencing of target genes in liver and brain in mice through expression of small interfering RNA (siRNA) has been established (Xia et al., 2002). These systems can be adapted to generate knockdown mice or knocking down c-jun and junB in the epidermis of mice, e.g. by designing siRNA constructs that are expressed in the epidermis of mice after delivery by means of suitable gene delivery protocols.

In a further aspect, the invention relates to keratinocytes derived from a mouse which is deficient for c-Jun and JunB in the epidermis (jun$^{\Delta ep^*}$, junB$^{\Delta ep^*}$) or from a mouse in which deletion of c-Jun and JunB can be specifically induced in the epidermis.

Keratinocytes can be obtained according to known methods, e.g. by using a protocol as described by or by Carroll et al., 1995, Carroll and Molès, 2000, or the following protocol (described in U.S. Pat. No. 6,566,136):

Sections of skin obtained from sacrificed mice that have been shaved and washed are separated in dermis and epidermis, e.g. by treatment with trypsin, for example by flotation of the samples of skin tissue in a trypsin solution (for example about 0.5%) during a time sufficient to provoke cell separation. The dermis is separated and the epidermis is subsequently placed in a medium for achieving a suspension. The medium for achieving a suspension may contain a solution of soy trypsin inhibitor (SBTI) and is put in contact with the cells for a time sufficient to inactivate the trypsin and to provoke the release of the cells. The cells are grown in a serum-free tissue culture medium and filtered in order to obtain the desired keratinocytes.

The resulting primary keratinocytes are subsequently seeded, in a suitable cell concentration, e.g. about $1.2 \times 10^4$ cells/cm$^2$, on previously coated culture plates. The culture plates are usually coated with a composition that increases fixation and growth of keratinocytes, usually a solution containing fibronectin and of collagen type I.

It was surprisingly found in the experiments of the invention that mice, after induced epidermis-specific deletion of c-jun and junB (c-jun$^{\Delta ep*}$; junB$^{\Delta ep*}$ mice), develop a psoriasis-like disease reflecting the hallmarks of psoriasis in humans within 2 weeks after tamoxifen injection. This phenotype was only seen after deletion of both c-jun and junB, but not after epidermis-specific deletion of c-jun or junB alone.

Thus the invention relates, in a further aspect, to the use of c-jun$^{\Delta ep*}$, junB$^{\Delta ep*}$ mice as an animal model for psoriasis and psoriatic arthritis.

The present invention provides a unique mouse model recapitulating many of the histological and molecular characteristics seen in the skin and joints of psoriatic patients. The phenotype develops very rapidly with 100% efficiency. The disease is not characterized by a generalized inflammatory response, but is prominent to hairless areas of the skin (ears, paws and tail) reminiscent of the symmetrically distributed psoriatic lesions in humans which are well demarcated from adjacent symptom-less skin. The diseased epidermis mirrors the changes in the cytokine and chemokine network reported for psoriasis. Expression profiling revealed further evidence that the changes in gene expression resemble most of the documented genetic changes described for human psoriasis.

The c-jun$^{\Delta ep*}$, junB$^{\Delta ep*}$ mice of the invention and keratinocytes derived therefrom are useful for testing drugs against psoriasis and psoriatic arthritis in vivo.

For example, given the role for pro-inflammatory cytokines such as IL-1, IL-8 and TNF-α in the pathogenesis of psoriasis, the mice of the invention may be utilized to evaluate specific inhibitors of these cytokine pathways or to test compounds whether they have an inhibitory effect. A specific illustration is the evaluation of inhibitors of the TNF-α pathway. For instance, c-jun$^{f/f}$, junB$^{f/f}$ K5-Cre-ER mice are treated with tamoxifen to obtain jun$^{\Delta ep*}$, junB$^{\Delta ep*}$ mice that develop the psoriasis-like disease. Upon first observation of symptoms, e.g. skin abnormality, the mice receive an inhibitor of this cytokine, e.g. a monoclonal antibody against mouse TNF-α, a well documented inhibitor of this cytokine in vivo. The mice are then be observed for the progression of skin lesions and the extent of disease progression can be compared to placebo-treated animals. Novel inhibitors of the TNF-α pathway, such as decoy receptors, TNF-synthesis inhibitors, MAP kinase inhibitors or therapeutic siRNA can also be used and the effects of treatment can be compared to anti-TNF-α treated animals. Likewise, test compounds, e.g. from compound libraries, can be applied to the animals and the effect of the compounds evaluated. The extent of lesion development post-treatment as well as the histopathologic makeup of the lesion can be analyzed (Carroll et al., 1995). Also the effect of compounds on disease induction can be determined by treating c-jun$^{f/f}$, junB$^{f/f}$ K5-Cre-ER mice prior to tamoxifen administration. Changes in systemic markers of inflammation, such as cytokine levels, acute phase proteins, lymphocyte subsets and immunoglobulin levels and isotypes can be evaluated. The extent of inflammation pre- and post-treatment may also be assessed through determining the vascular permeability of diseased skin using extravasation markers such as Evans blue dye or 125I labeled albumin.

The animal model of the invention is not limited to the evaluation of inhibitors of pro-inflammatory cytokines. For instance, novel inhibitors of leukocyte trafficking, such as adhesion molecules or chemokines, can be tested in the model similar to the aforementioned protocol. Also, specific inhibitors of the immune system such as inhibitors of T-cell activation, cytokine production or co-stimulation can be used. Agents or methods aimed at the induction of T regulatory cells can also be assessed.

Finally, the animal model of the invention is useful to test the effect of modulators directed specifically against keratinocyte function or other cells of the skin. Such agents can be evaluated both in vivo and in vitro. For instance, animals can be induced for disease as described above and keratinocyte/skin specific agents applied via topical or systemic routes. The effect of such agents, or test compounds, on lesion development can be measured via histopathologic analysis (Carroll et al., 1995) and compared to untreated animals. Likewise, primary keratinocyte cultures or keratinocyte lines can be established in vitro from diseased animals using standard protocols (Carroll et al., 1995). Test compounds can be administered to the cultured cells in various doses and the effect on keratinocyte proliferation, viability, morphology and cytokine/growth factor production can be evaluated. Furthermore, cultured double knock-out keratinocytes, which can be obtained from the mice of the invention according to standard protocols, e.g. as described by Carroll et al. 1995; Carroll and Molès, 2000; Zenz et al., 2003, or in vitro skin tissue equivalents (Szabowski et al., 2000) or three-dimensional skin culture models (Carroll and Molés, 2000) can be used to screen for drugs inhibiting the production of keratinocytes-derived growth factors and cytokines responsible for psoriasis.

EXAMPLES

In the Examples, the following materials and methods were used:

Generation of junB$^{f/f}$ Mice

A floxed and frt-flanked neomycin resistance and thymidine kinase gene selection cassette was inserted into a SmaI site present in the 5' untranslated region (UTR) of junB. The 3' loxP site was inserted into the XhoI site, 161 bp downstream of the translation stop codon. A diphtheria toxin gene was included for selection against random integrants. The linearized targeting construct was electroporated into HM-1 ES cells and the identification of homologous recombinants by PCR using two sets of primers was performed as described previously (Schorpp-Kistner et al., 1999). The neomycin and thymidine kinase genes were deleted by transient transfection of a vector expressing flp recombinase. Two ES cell clones carrying a floxed allele of junB were injected into C57BL/6 blastocysts and several chimeras from one ES cell clone transmitted the mutant allele to their offspring.

Generation of c-jun$^{\Delta ep*}$; junB$^{\Delta ep*}$ Mice

Mice carrying a foxed c-jun allele (c-jun$^{f/f}$; Behrens et al., 2002) were crossed to mice carrying a foxed junB allele (junB$^{f/f}$, Kenner et al., 2004) to obtain mice double-floxed mice (c-jun$^{f/f}$; junB$^{f/f}$). Double foxed mice were crossed to transgenic mice expressing the Cre recombinase estrogen receptor fusion under the control of the keratinocyte-specific Keratin 5 promoter (K5-Cre-ER; Brocard et al., 1997) to obtain c-jun$^{f/f}$; junB$^{f/f}$ and c-jun$^{f/f}$; junB$^{f/f}$; K5-Cre-ER mice.

Inducible Deletion of c-jun$^{f/f}$ and junB$^{f/f}$ 8 weeks old experimental mice (c-jun$^{f/f}$; junB$^{f/f}$; K5-Cre-ER) and control mice (c-jun$^{f/f}$; junB$^{f/f}$) were injected intraperitoneally 5 times with 1 mg tamoxifen (Sigma; Vasioukhin et al., 1999).

Southern Blot and RNase Protection Assay (RPA)

For the c-jun Southern blot, 10 µg of epidermal DNA was digested with XbaI (for c-jun) yielding a 6.9 kb fragment for the floxed c-jun allele and a 3.3 kb fragment for the deleted c-jun allele (Behrens et al., 2002). For the junB Southern 10 µg of genomic DNA was digested with PstI yielding a 2.3 kb fragment for the floxed junB allele and a 0.7 kb fragment for the deleted junB allele. For detection of the bands a 176 bp PstI/HindIII fragment of junB was used as probe (Kenner et al., 2004). For the RNase protection assay total epidermal RNA was isolated with the TRIZOL protocol (Sigma). RNase protection assays were performed using the Ribo-Quant multi-probe RNase protection assay systems mJun/Fos (PharMingen) according to the manufacturer's protocol.

Histology

Tissues were fixed overnight with neutral buffered 4% PFA at 4° C. and either directly or after decalcification (bone) in 0.5% EDTA for 12 days embedded in paraffin. Five-micrometer sections were stained either with hematoxylin and eosin (H&E) or processed further. Immunohistochemical staining for anti CD3 and F4/80 (Santa Cruz) was performed after antigen-retrieval (Dako S1699) with the MultiLink Dako system (Dako E0453) according to the manufacturer's recommendations.

Example 1

Figure 1:
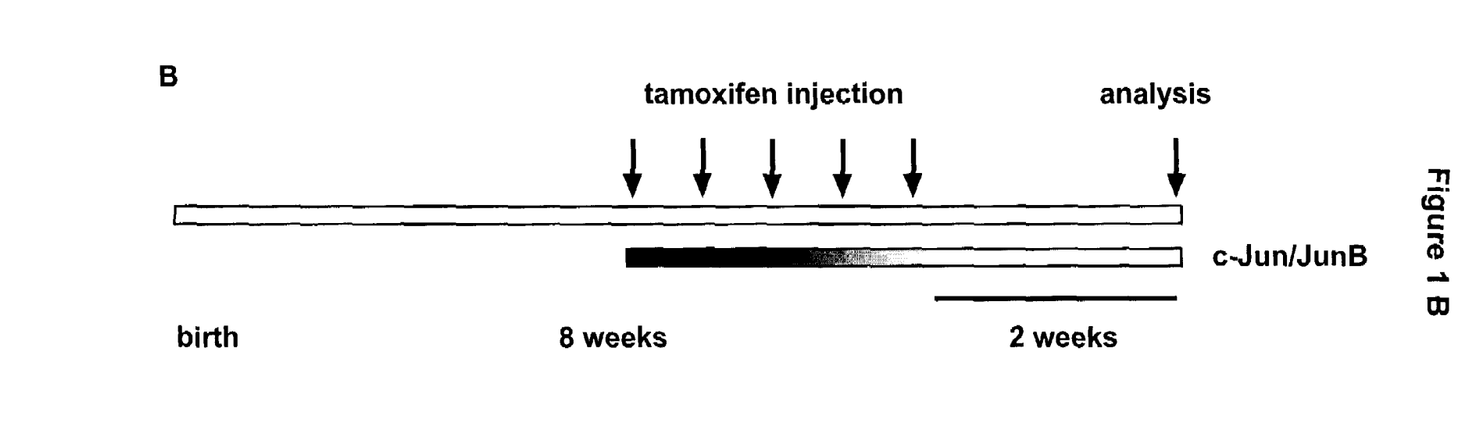
Figure 1A:
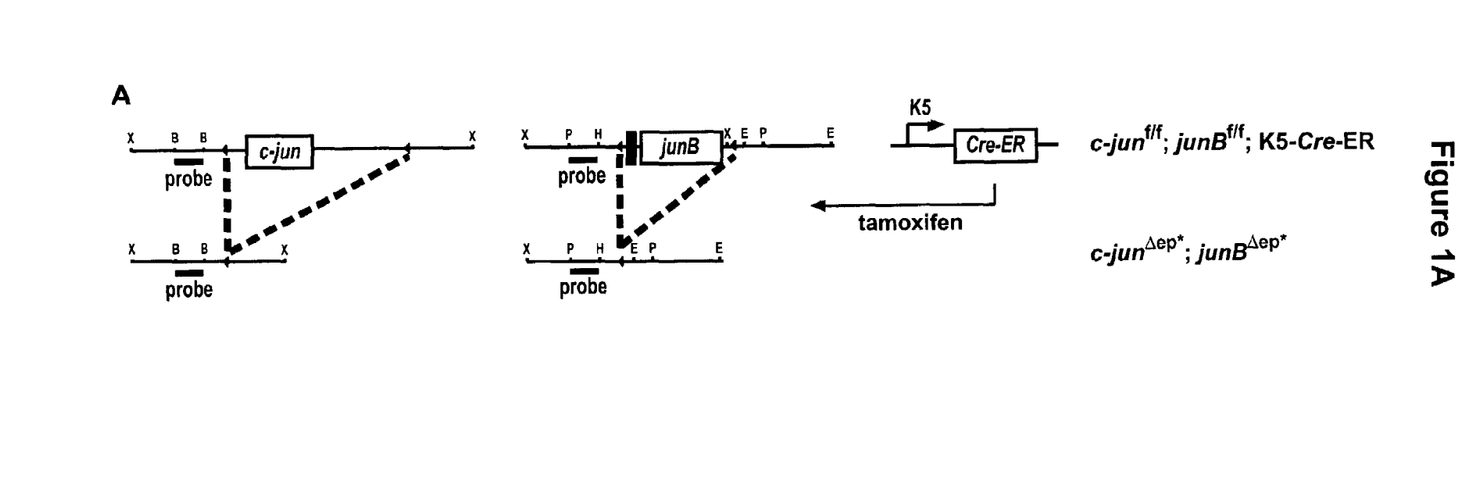
Figure 1C:
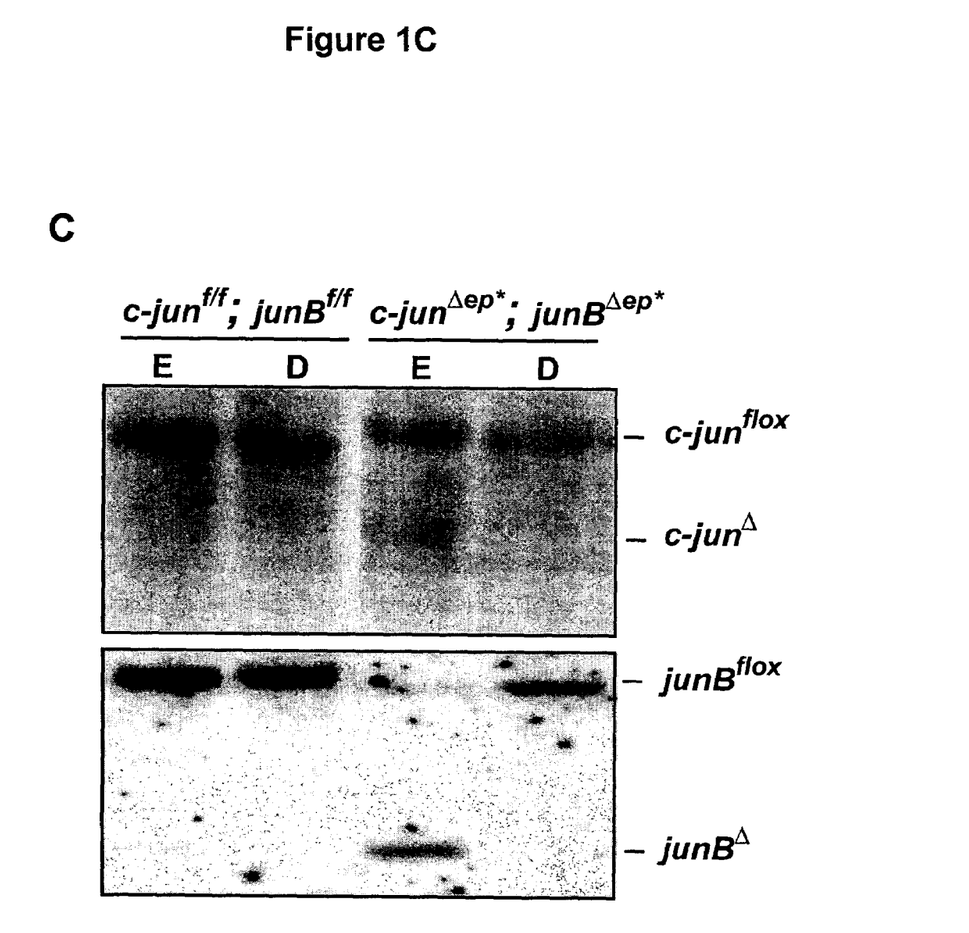
Figure 1D:
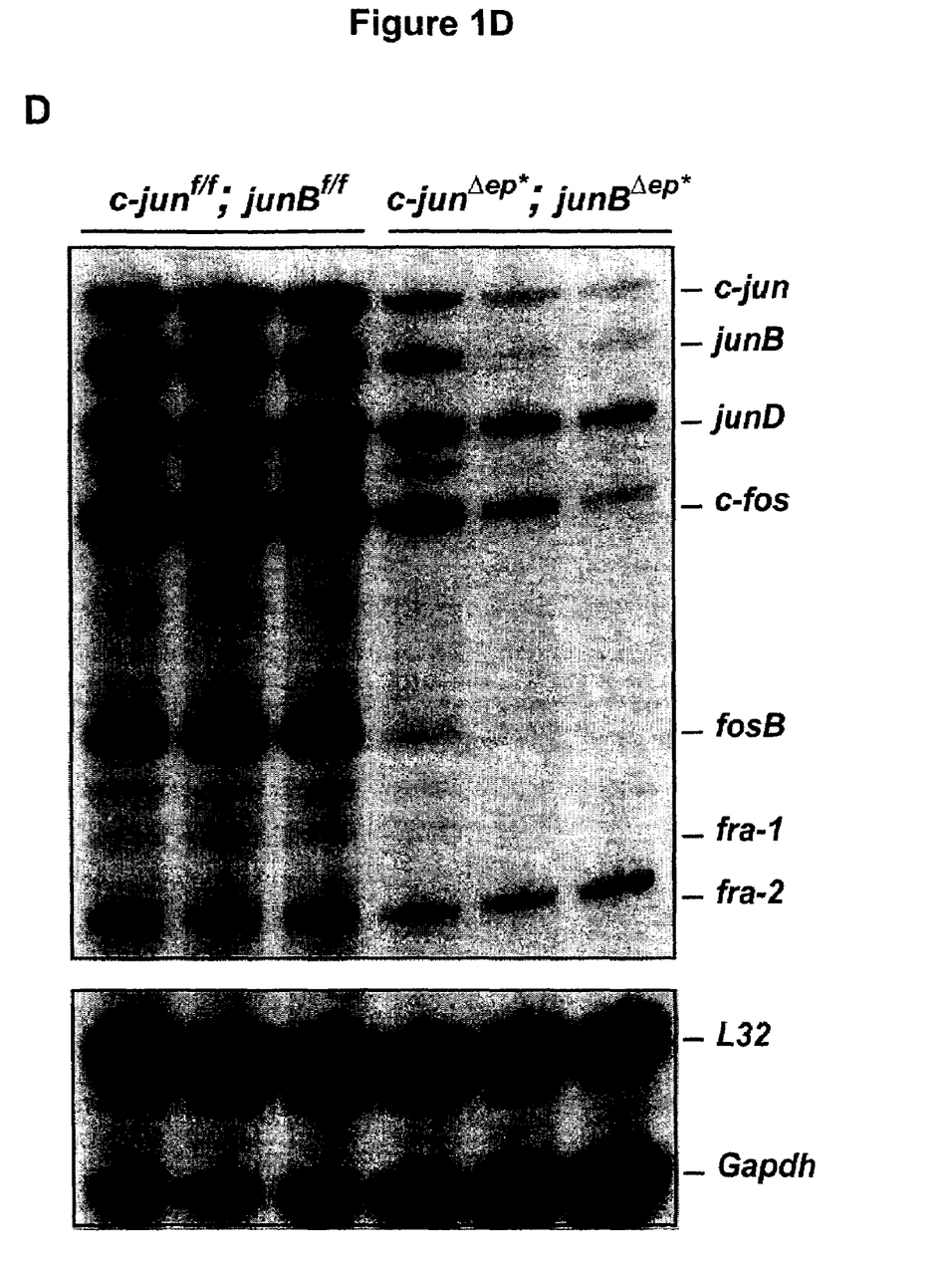

Generation of c-jun$^{\Delta ep*}$; junB$^{\Delta ep*}$ Mice c-jun$^{f/f}$; junB$^{f/f}$ mice were crossed to K5-Cre-ER transgenic mice and heterozygous progenies were intercrossed to get c-jun$^{f/f}$; junB$^{f/f}$; K5-Cre-ER and c-jun$^{f/f}$; junB$^{f/f}$ mice. The approach to delete c-jun and junB in the epidermis is outlined in FIGS. 1A and 1B. In brief, 8 weeks old experimental mice (c-jun$^{f/f}$; junB$^{f/f}$; K5-Cre-ER) and control mice (c-jun$^{f/f}$; junB$^{f/f}$) were injected intraperitoneally 5 times with 1 mg tamoxifen. 2 weeks after the last injection the mice were analyzed. The deletion of c-jun and junB was analyzed by Southern blot and RPA (RNAse protection assay). Southern blot analyses for c-jun and JunB deletion (FIG. 1C) showed deletion in both cases. The remaining signal for floxed c-jun and floxed junB is explained by incomplete deletion and the inflammatory infiltrate seen in the epidermis of c-jun$^{\Delta ep*}$; junB$^{\Delta ep*}$ mice (FIG. B). Quantification of AP-1 mRNA in the epidermis of c-jun$^{\Delta ep*}$; junB$^{\Delta ep*}$ mice showed significant down regulation of c-jun and junB mRNA and also for other AP-1 genes except fra2.

Example 2

Characterization of c-jun$^{\Delta ep*}$; junB$^{\Delta ep*}$ Mice

Figure 2A:
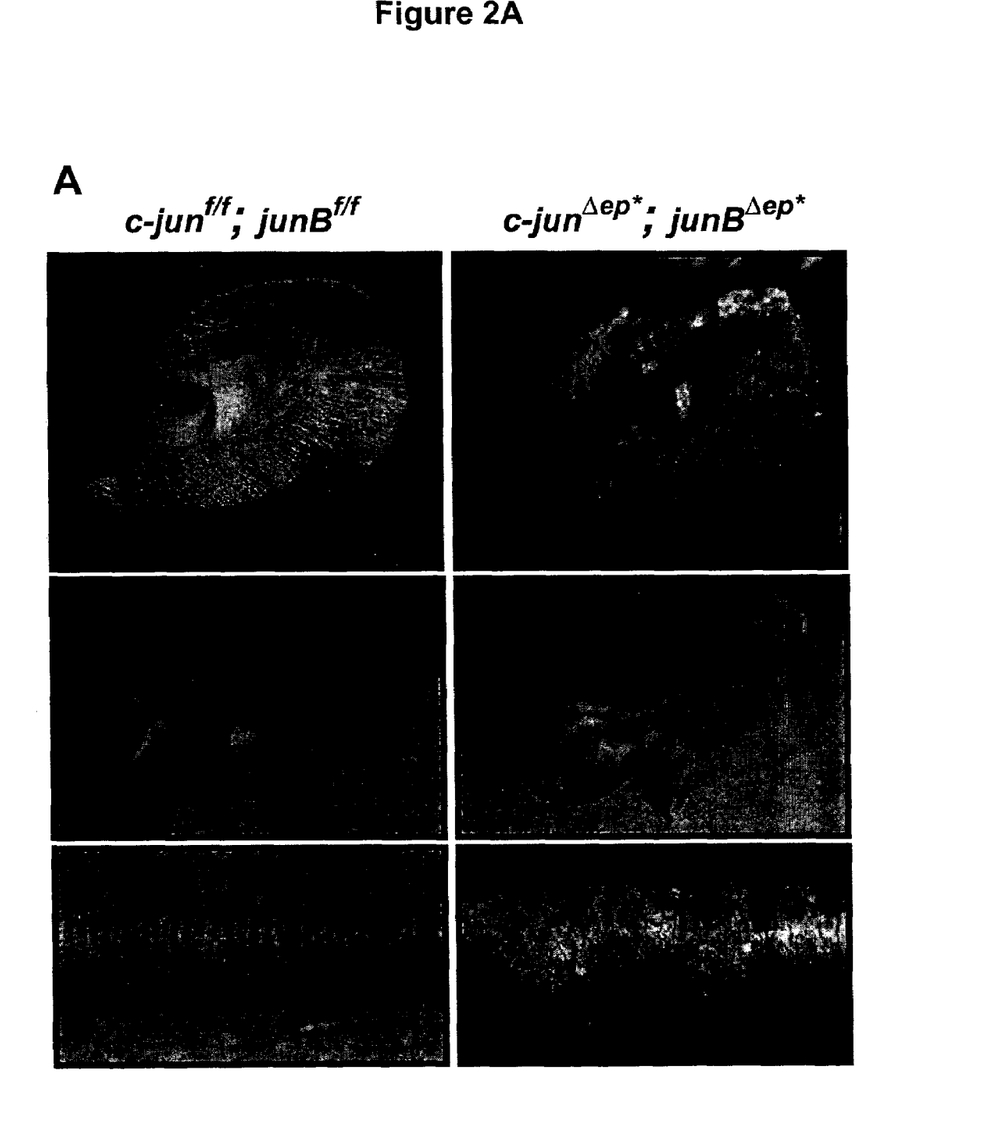
Figure 2B:
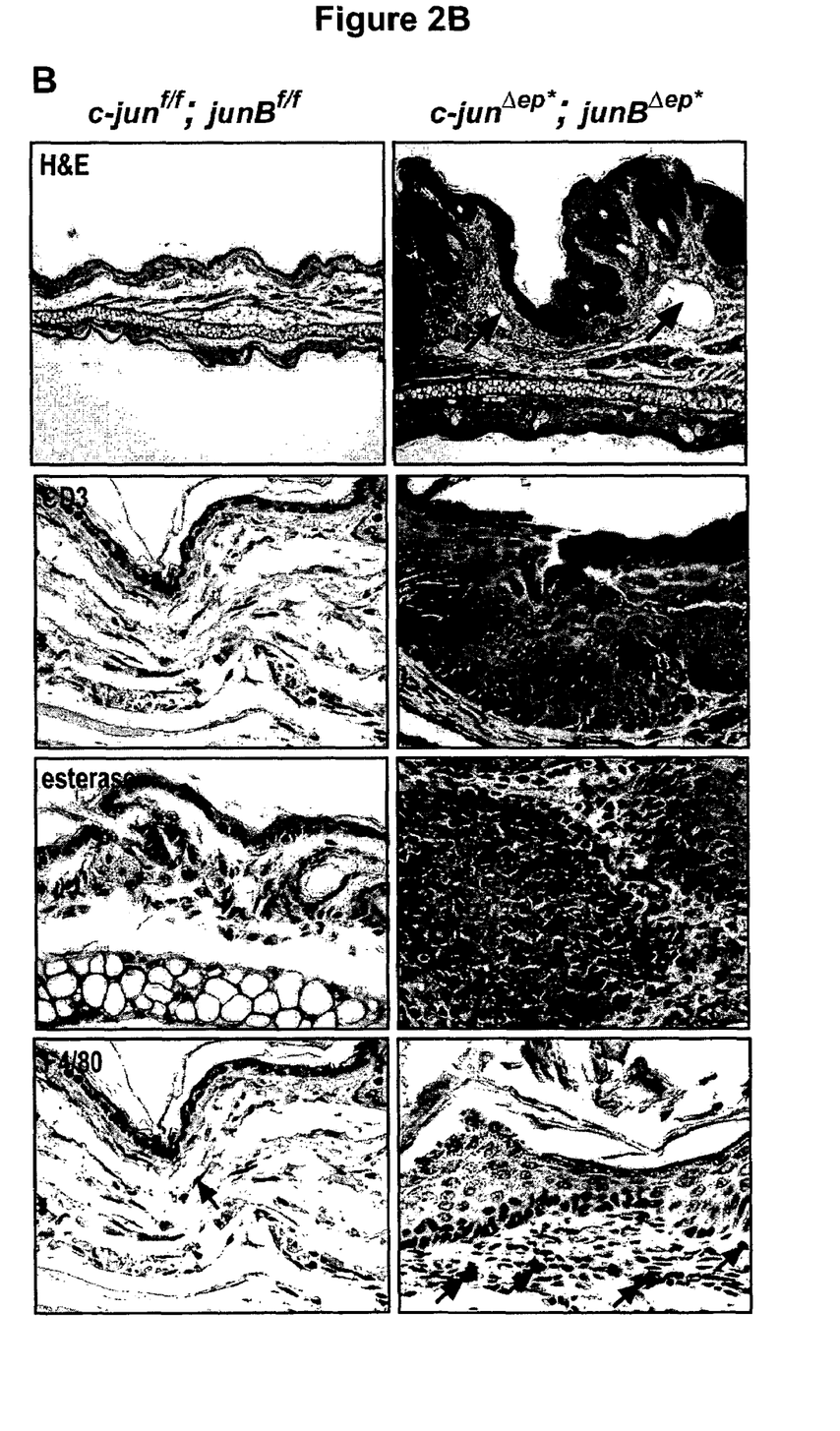
Figure 2C:
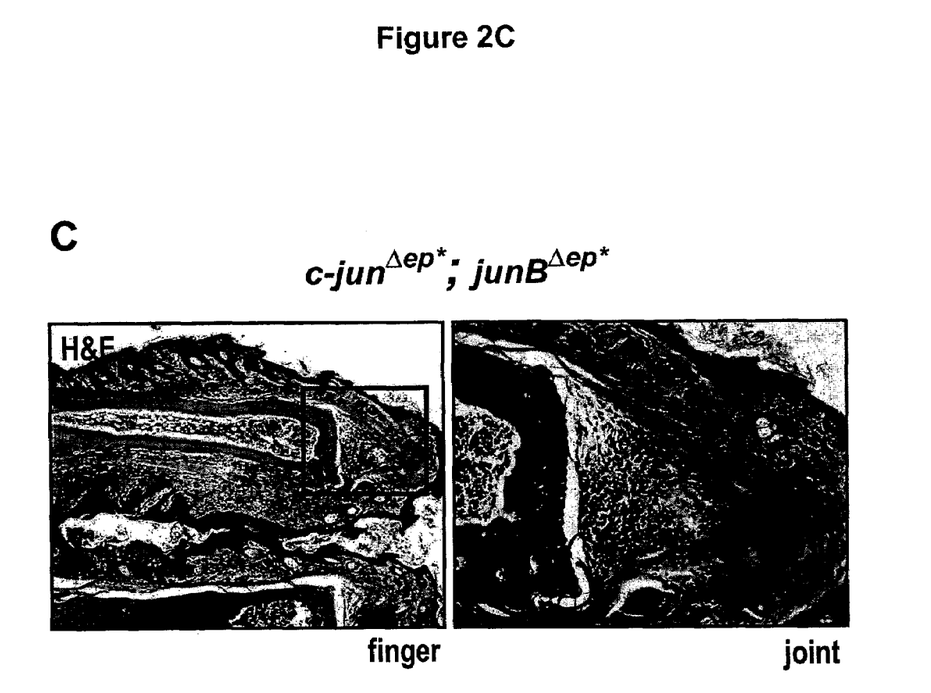

Mice obtained according to the treatment described in Example 1 develop a phenotype resembling psoriasis within 2 weeks. Hairless skin like ear, tail and feet were dramatically affected (FIG. 2A). Histological examination (FIG. 2B) revealed abnormally thickened epidermis, parakeratosis (nucleated keratinocytes in the cornified layer), thickened keratinized upper layer (hyperkeratosis), and fingerlike epidermal projections into the dermis (rete ridges). Furthermore, epidermal microabscesses and the typical inflammatory cell infiltrate are seen: intraepidermal T-cells (CD3 staining), increased numbers of neutrophils in the epidermis (esterase staining), and macrophages in the dermis (esterase- and F4/80-staining). H&E staining from affected mouse finger demonstrating granulocytic infiltrates into the joint region resembling psoriatic arthritis (FIG. 2C).

REFERENCES

Baichwal V. R. and Tjian R. (1990). Control of c-Jun activity by interaction of a cell-specific inhibitor with regulatory domain d: Differences between v- and c-Jun. Cell 63, 815-25.

Behrens A., Sibilia M., David J P., Mohle-Steinlein U., Tronche F., Schutz G., Wagner E F. (2002). Impaired postnatal hepatocyte proliferation and liver regeneration in mice lacking c-jun in the liver. EMBO J. 21, 1782-90.

Bohmann D. and Tjian R. (1989). Biochemical analysis of transcriptional activation by Jun: Differential activity of c- and v-Jun. Cell 59, 709-17.

Boyle W. J., Smeal T., Defize L. H. K., Angel P., Woodgett J. R., Karin M., and Hunter T. (1991). Activation of protein kinase C decreases phosphorylation of c-Jun at sites that negatively regulate its DNA-binding activity. Cell 64, 573-584.

Branda C. S. and Dymecki S. M. (2004). Talking about a Revolution. The impact of site-specific recombinases on genetic analyses in Mice. Dev. Cell 6(1):7-28.

Brocard J., Warot X., Wendling O., Messaddeq N., Vonesch J L., Chambon P., Metzger D. (1997). Spatio-temporally controlled site-specific somatic mutagenesis in the mouse. Proc. Natl. Acad. Sci. 94, 14559-63.

Carroll J M., Luetteke N C., Lee D C., Watt F M. (1995). Suprabasal integrin expression in the epidermis of transgenic mice results in developmental defects and a phenotype resembling psoriasis. Cell 83:957-968.

Carroll J M, Molès J P. (2000) A three-dimensional skin culture model for mouse keratinocytes: application to transgenic mouse keratinocytes. Exp Dermatol 2000: 9: 20-24.

Chiu R., Angel P., Karin M. (1989). Jun-B differs in its biological properties from, and is a negative regulator of, c-Jun. Cell 59, 979-86.

Danielian P S., White R., Hoare S A., Fawell S E., Parker M G. (1993). Identification of residues in the estrogen receptor that confer differential sensitivity to estrogen and hydroxytamoxifen. Mol Endocrinol 7(2):232-40.

Deng T., Karin M. (1993). JunB differs from c-Jun in its DNA-binding and dimerization domains, and represses c-Jun by formation of inactive heterodimers. Genes Dev. 7(3):479-90.

Du W., Thanos D., and Maniatis T. (1993). Mechanisms of transcriptional synergism between distinct virus-inducible enhancer elements. Cell 74, 887-98.

Eferl, R. and Wagner, E. F. (2003). AP-1: A double-edged sword in tumorigeneis. Nature Reviews Cancer 3, 859-868.

Herrlich P. and Ponta H. (1989). "Nuclear" oncogenes convert extracellular stimuli into changes in the genetic program. Trends Genet. 5: 112-5.

Imler J. L., Ugarte E., Wasylyk C. and Wasylyk B. (1988) v-jun is a transcriptional activator, but not in all cell lines. Nucleic Acids Res. 16, 3005-12.

Hilberg F., Agguzi A., Howells N., and Wagner E. F. (1993). c-Jun is essential for normal mouse development and hepatogenesis. Nature 365, 179-181.

Jiang C K., Epstein H S., Tomic M., Freedberg I M. and Blumenberg M. (1991). Functional comparison of the upstream regulatory DNA sequences of four human epidermal keratin genes. J. Invest. Dermatol., Vol 96, 162-167.

Johnson R. S., van Lingen B., Papaioannou V. E., and Spiegelman B. M. (1993). A null mutation at the c-jun locus causes embryonic lethality and retarded cell growth in culture. Genes Dev. 7, 1309-1317.

Karin M. and Smeal T. (1992). Control of transcription factors by signaling transduction pathways: The beginning of the end. Trends Biochem. Sci. 17, 418-22.

Kenner L, Hoebertz A, Beil T, Keon N, Karreth F, Eferl R, Scheuch H, Szremska A, Amling M, Schorpp-Kistner M, Angel P, Wagner E F. (2004): Mice lacking JunB are osteopenic due to cell-autonomous osteoblast and osteoclast defects. J Cell Biol. 164(4):613-23.

Kunath T., Gish G., Lickert H., Jones N., Pawson T., Rossant J. (2003). Transgenic RNA interference in ES cell derived embryos recapitulates a genetic null phenotype. Nat. Biotchnol. 21(5): 559-61

Lebwohl M (2003). Psoriasis. Lancet 361(9364):1197-204

Li B., Tournier C., Davis R J., Flavell R A. (1999). Regulation of IL-4 expression by the transcription factor JunB during T helper cell differentiation. EMBO 18(2):420-32.

Li G., Gustafson-Brown C., Hanks S K., Nason K., Arbeit J M., Pogliano K., Wisdom R M., Johnson R S. (2003). c-jun is essential for organization of the epidermal leading edge. Dev. Cell 4(6): 865-77.

Lin A., Frost J., Deng T., Smeal T., al-Alawi N., Kikkawa U., Hunter T., Brenner D., and Karin M. (1992). Casein kinase II is a negative regulator of c-Jun DNA binding and AP-1 activity. Cell. 70, 777-89.

Minamino T, Gaussin V, DeMayo F J, Schneider M D (2001). Inducible gene targeting in postnatal myocardium by cardiac-specific expression of a hormone-activated Cre fusion protein. Circ Res. March 30; 88(6): 587-92

Nickoloff B J., von den Driesch P., Raychaudhuri S P., Boehncke W-H., Morhenn V B., Farber E M., Holik M F., Schröder J M. (2000). Is psoriasis a T-cell disease? Exp Dermatol 9: 359-375.

Pulverer B. J., Kyriakis J. M., Avruch K., Nikolakaki E., and Woodgett J. R. (1991). Phosphorylation of c-jun mediated by MAP kinases. Nature 353, 670-674.

Ransone L. J. and Verma I. M. (1990). Nuclear proto-oncogenes Fos and Jun. Annu. Rev. Cell Biol. 6, 539-57.

Sachsenmaier C. and Radler-Pohl A. (1994). Regulation of c-Jun activity by phosphorylation. In: The fos and jun families of transcription factor/edited by Peter E. Angel and Peter A. Herrlich. CRC Press. pp. 61-70.

Schön M P (1999). Animal models of psoriasis—what can we learn from them? J Invest Dermatol. 112(4):405-10

Schorpp-Kistner M., Wang Z Q., Angel P., Wagner E F. (1999). JunB is essential for mammalian placentation. EMBO J. 18(4):934-48.

Stein B., Baldwin A. S. Jr., Ballard D., Greene A, Angel P. and Herrlich P. (1993). Cross-coupling of the NF(Bp65 and Fos/Jun transcription factors produces potentiated biological functions. EMBO J. 12, 3879-91.

Szabowski A., Mass-Szabowski N., Andrecht S., Kolbus A., Schorpp-Kistner M., Fusenig N E., Angel P. (2000). c-Jun and junB antagonistically control cytokine-regulated mesenchymal-epidermal interaction in skin. Cell 103(5): 745-55

Vasioukhin V., Degenstein L. Wise B., Fuchs E. (1999). The magic touch: Genome targeting in epidermal stem cells induced by tamoxifen application to mouse skin. Proc. Natl. Acad. Sci. 96: 8551-8556.

Xia H., Mao Q., Paulson H. L., Davidson B. L. (2002) siRNA-mediated gene silencing in vitro and in vivo. Nat. Biotechnol. 20(10): 1006-10.

Xia Y P., Li B., Hylton D., Detmar M., Yancopoulos G D., Rudge J S. (2003) Transgenic delivery of VEGF to mouse skin leads to an inflammatory condition resembling human psoriasis. Blood 102(1):161-8.

Zenz R., Scheuch H., Martin P., Frank C., Eferl R., Kenner L., Sibilia M., Wagner E F. (2003). c-Jun regulates eyelid closure and skin tumor development trough EGFR signaling. Dev. Cell 4(6): 879-89.

What is claimed is:

1. A transgenic mouse whose genome comprises deletions of c-Jun and JunB genes in keratinocytes of the epidermis, wherein said transgenic mouse is a double knockout for said c-Jun and JunB genes in keratinocytes of the epidermis following keratinocyte-specific activation and expression of a site-specific recombination enzyme, and wherein said transgenic mouse exhibits one or more characteristics selected from the group consisting of an abnormally thickened epidermis, parakeratosis, hyperkeratosis, fingerlike epidermal projections into the dermis, granulocytic infiltrates into the joint region, rete ridges, epidermal microabscesses, intraepidermal T-cells, increased numbers of neutrophils, macrophages in the dermis, or combinations thereof.

2. The mouse of claim 1, in which deletion of c-Jun and JunB genes can be specifically and conditionally induced in keratinocytes of the epidermis.

3. The mouse of claim 1, in which deletion of c-Jun and JunB genes is achieved by expression of a constitutively active or inducible recombination enzyme in keratinocytes of the epidermis.

4. A method for obtaining a mouse of claim 3, wherein a transgenic mouse having c-Jun and JunB genes flanked with recognition sites for a site specific recombination enzyme is crossed with a transgenic mouse expressing a constitutively active or inducible recombinase in keratinocytes of the epidermis.

5. The method of claim 4, wherein the site-specific recombination enzyme is Cre-recombinase, which is fused to the estrogen receptor, under the transcriptional control of a keratinocyte-specific promoter.

6. A method for obtaining a mouse of claim 1, wherein a transgenic mouse having the c-Jun and JunB genes flanked with recognition sites for a site-specific recombination enzyme is crossed with a transgenic mouse expressing a constitutively active or inducible recombinase in the epidermis, and deletion of c-Jun and JunB genes is specifically induced in keratinocytes of the epidermis.

7. The method of claim 6, wherein the recognition sites are loxP sites and the site-specific recombination enzyme is Cre-recombinase, which is fused to the estrogen receptor, under the transcriptional control of a keratinocyte-specific promoter, and wherein keratinocyte-specific deletion of c-Jun and JunB genes is induced by applying an anti-estrogen.

8. The method of claim 7, wherein the anti-estrogen is applied by intraperitoneal injection or topical application.

9. The method of claim 7, wherein the anti-estrogen is tamoxifen.

10. Keratinocytes derived from a mouse of claim 1, wherein said keratinocytes are double knockouts for c-Jun and JunB genes.

11. The mouse of claim 1, wherein said one or more characteristics is a combination of an abnormally thickened epidermis, parakeratosis, hyperkeratosis, and rete ridges.

12. The mouse of claim 1, wherein said one or more characteristics is granulocytic infiltrates into the joint region.

13. The mouse of claim 3, wherein c-Jun and Jun-B genes are flanked with recognition sites for a site specific recombination enzyme.

14. The mouse of claim 13, wherein said recognition sites are loxP sites and said site-specific recombination enzyme is Cre-recombinase.

15. The mouse of claim 14, wherein said Cre-recombinase is fused to an estrogen receptor, under the transcriptional control of a keratinocyte-specific promoter.

16. A method comprising
(a) administering an agent to a transgenic mouse whose genome comprises deletions of c-Jun and JunB genes in keratinocytes of the epidermis, wherein said transgenic mouse is a double knockout for said c-Jun and JunB genes in keratinocytes of the epidermis following keratinocyte-specific activation and expression of a site-specific recombination enzyme, and wherein said transgenic mouse exhibits one or more characteristics selected from the group consisting of an abnormally thickened epidermis, parakeratosis, hyperkeratosis, fingerlike epidermal projections into the dermis, granulocytic infiltrates into the joint region, rete ridges, epidermal microabscesses, intraepidermal T-cells, increased numbers of neutrophils, macrophages in the dermis, or combinations thereof; and
(b) measuring the effect of said agent on said one or more characteristics of said mouse.

17. The method of claim 16, wherein said agents are administered topically or systemically.

18. A method comprising
(a) administering an agent to keratinocytes derived from a transgenic mouse of claim 1; and
(b) measuring the effect of said agent on the proliferation, viability, morphology, cytokine production, growth factor production or molecular characteristics of said keratinocytes.

19. The method of claim 18, wherein said agent is an inhibitor of the production of keratinocyte-derived growth factors and/or cytokines associated with psoriasis.

* * * * *